US009126889B2

(12) United States Patent
Nair et al.

(10) Patent No.: US 9,126,889 B2
(45) Date of Patent: Sep. 8, 2015

(54) FLUOROSURFACTANTS HAVING IMPROVED BIODEGRADABILITY

(71) Applicant: Honeywell International Inc., Morristown, NJ (US)

(72) Inventors: Haridasan K. Nair, Williamsville, NY (US); Yian Zhai, Williamsville, NY (US); Andrew J. Poss, Kenmore, NY (US); Rajiv R. Singh, Getzville, NY (US); David Nalewajek, West Seneca, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 0 days.

(21) Appl. No.: 14/459,375

(22) Filed: Aug. 14, 2014

(65) Prior Publication Data

US 2015/0065746 A1    Mar. 5, 2015

Related U.S. Application Data

(60) Provisional application No. 61/873,675, filed on Sep. 4, 2013.

(51) Int. Cl.
| | | |
|---|---|---|
| *C11D 3/37* | (2006.01) |
| *C11D 3/24* | (2006.01) |
| *C09D 11/00* | (2014.01) |
| *C07C 21/18* | (2006.01) |
| *C07C 57/03* | (2006.01) |
| *C07C 43/178* | (2006.01) |
| *C07C 309/06* | (2006.01) |
| *C07C 323/25* | (2006.01) |
| *C07C 229/12* | (2006.01) |
| *C08F 14/18* | (2006.01) |
| *C08F 214/18* | (2006.01) |
| *C07C 41/03* | (2006.01) |

(52) U.S. Cl.
CPC ............... *C07C 21/18* (2013.01); *C07C 41/03* (2013.01); *C07C 43/1786* (2013.01); *C07C 57/03* (2013.01); *C07C 229/12* (2013.01); *C07C 309/06* (2013.01); *C07C 323/25* (2013.01); *C08F 14/18* (2013.01); *C08F 214/18* (2013.01)

(58) Field of Classification Search
CPC ........................................................ C07C 21/18

USPC ............ 562/605; 560/115, 129, 22, 227, 605
See application file for complete search history.

(56) References Cited

U.S. PATENT DOCUMENTS

| | | | |
|---|---|---|---|
| 6,013,795 A | 1/2000 | Manzara et al. |
| 6,015,838 A | 1/2000 | Stern et al. |
| 7,030,067 B2 | 4/2006 | Lamanna et al. |
| 7,511,008 B2 | 3/2009 | Scheuing et al. |
| 7,696,262 B2 | 4/2010 | Cagle et al. |
| 8,008,358 B2 | 8/2011 | Kirsch et al. |
| 8,049,022 B2 | 11/2011 | Hierse et al. |
| 8,049,040 B2 | 11/2011 | Qiu et al. |
| 8,067,625 B2 | 11/2011 | Hierse et al. |
| 2009/0197201 A1 | 8/2009 | Hierse et al. |
| 2009/0320718 A1 | 12/2009 | Hierse et al. |
| 2010/0152081 A1 | 6/2010 | Hierse et al. |
| 2012/0113195 A1 | 5/2012 | Katsuragi |
| 2012/0252949 A1 | 10/2012 | Hintzer et al. |
| 2013/0172476 A1 | 7/2013 | Sasamoto et al. |

FOREIGN PATENT DOCUMENTS

| | | | |
|---|---|---|---|
| WO | WO 2007/140112 A1 | 12/2007 |
| WO | WO 2010/090269 A1 | 8/2010 |
| WO | WO 2010/110339 A1 | 9/2010 |
| WO | WO 2012/074196 A2 | 6/2012 |
| WO | WO 2012/101545 A1 | 8/2012 |

OTHER PUBLICATIONS

Fromel et al, Chemosphere (2010), vol. 80 (11), pp. 1387-1392.*
Kostov et al., Journal of Fluorine Chemistry, vol. 130, pp. 1192-1199 (2009).
S. Dimitrov, et al., Predicting the Biodegradation Products of Perfluorinated Chemicals Using Catabol, SAK and QSAR in Environmental Research, vol. 15(1) Feb. 2004, pp. 69-82.
Natalia Quinete, et al.,Degradation Studies of New Substitutes for Perfluorinated Surfactants, Archenviron Contam Toxicol 59, Jan. 7, 2010, pp. 20-30.
John R.Parsons et al., Biodegradation of Perfluorinated Compounds, Rev Environ Contam Toxicol, 196, 2008 pp. 53-71.

* cited by examiner

*Primary Examiner* — Kamal Saeed
*Assistant Examiner* — Janet L Coppins

(57) ABSTRACT

To address the problem of insufficient biodegradability of perfluorinated surfactants, the present invention provides biodegradable fluorosurfactants derived from olefins having —CHR, —CHRf, —CHF, and/or —CH$_2$ groups, where R is an alkyl group and Rf is a perfluoro or fluroroalkyl group. Preferably, the —CHR, —CHRf, —CHF, and/or —CH$_2$ groups are contained within partially fluorinated alkenes.

19 Claims, No Drawings

FLUOROSURFACTANTS HAVING IMPROVED BIODEGRADABILITY

CROSS-REFERENCE TO RELATED APPLICATION

This application claims domestic priority from commonly owned U.S. Provisional Application Ser. No. 61/873,675 filed 4 Sep. 2013, the disclosure of which is hereby incorporated herein by reference.

FIELD OF THE INVENTION

The present invention relates to the production of fluorosurfactants having improved biodegradability. More specifically, the present invention relates to biodegradable fluorosurfactants produced from olefins comprising —CHR, —CHRf, —CHF, and/or —CH$_2$ groups, wherein R is an alkyl group and Rf is a perfluoro or fluroroalkyl group.

BACKGROUND OF THE INVENTION

Fluorosurfactants have many unique properties, and are useful as soil and water repellents, airplane hydraulic fluids, additives in firefighting foams, paints, coatings, clothing, carpets, leather, waxes, polishes, and the like. Fluorosurfactants like perfluorooctanoic acid (PFOA) are also used as surfactants in aqueous media for the polymerization of hydrophobic monomers, especially fluorinated monomers such as tetrafluoroethylene. See Erik Kissa, Fluorinated Surfactants and Repellents, Surfactant Science Series, Vol. 97, 2nd edition (2001) ("Kissa"). The most commonly used fluorosurfactants are perfluorooctanoic acid (PFOA, C$_7$F$_{15}$CO$_2$H) and perfluorooctane sulfonate (PFOS, C$_8$F$_{17}$SO$_3$X, X=K, Na, H).

Typically, fluorosurfactants are compounds having a hydrophobic (generally a perfluoroalkyl chain) and a hydrophilic moiety (generally carboxylate/sulfate/quaternary ammonium moiety, or the like). When the hydrophobic chain is a perfluoroalkyl group, such as the C$_7$F$_{15}$ or C$_8$F$_{17}$ groups of PFOA and PFOS, respectively, such compounds are highly resistant to biodegradation. However, the fluorosurfactants having such perfluoroalkyl hydrophobic chains are persistent, toxic, bioaccumulable, and accordingly are found in blood of many animals and humans all over the world. See, e.g., M. Houde et al., Environ. Sci. Tech. 40, (2006), 3463-3473; Boutevin, et al., J. Fluorine Chem. 134, (2012), 77-84. Accordingly, it is even possible that the United States Environmental Protection Agency (EPA) may eliminate the use of PFOA and PFOS in the near future owing to environmental concerns. There is thus a significant and urgent need in developing alternate fluorosurfactants that are biodegradable and environmentally friendly (see H. J. Lehmler, Chemosphere, 58, (2005), 1471-1496; G. Kostov et al., J. Fluorine Chem. 130, (2009), 1192-1199).

SUMMARY OF THE INVENTION

To address the problem of insufficient biodegradability, the present invention provides biodegradable fluorosurfactants derived from commercially available raw materials, i.e., from olefins comprising —CHR, —CHRf, —CHF, and/or —CH$_2$ groups.

Thus, one embodiment of the invention is a fluorosurfactant having the general formula Rf—X—Y, wherein Rf is a perfluorinated alkyl group, X is a fluoroolefin, Y is a neutral group, such as OH, or a hydrophilic group, and wherein the surfactant is biodegradable.

In certain embodiments, the fluorosurfactant of formula Rf—X—Y includes X which is derived from a partially fluorinated alkene.

In certain embodiments, the fluorosurfactant of formula Rf—X—Y includes a partially fluorinated alkene which is selected from the group consisting of CF$_2$=CFCl, CH$_2$=CHF, CHF=CHF, CH$_2$=CF$_2$, CF$_3$CH=CHCF$_3$, CF$_3$CF=CFCF$_3$, CF$_3$C=H, and (CF$_3$)$_2$CF—CF=CFCF$_3$ (HFP dimer).

In certain embodiments, the fluorosurfactant of formula Rf—X—Y includes X which is derived from a partially fluorinated propene.

In certain embodiments, the fluorosurfactant of formula Rf—X—Y includes a partially fluorinated propene which is selected from the group consisting of CF$_3$CF=CH$_2$ (HFO-1234yf), CF$_3$CH=CHF (HFO 1234ze), CF$_3$CF=CHF (HFO-1225yf), CF$_3$CH=CHCl (HCFO-1233zd), CF$_3$CH=CH$_2$, CF$_3$CH=CF$_2$, CF$_3$CF=CF$_2$, CF$_3$CHCH, (CF(CF$_3$)(CF$_2$H)H, and hexfluoropropene trimer.

In certain embodiments, the fluorosurfactant is an anionic surfactant.

In certain embodiments, the anionic surfactant is selected from the group consisting of carboxylates, sulfonates, sulfates, phosphates, and mixtures thereof.

In certain embodiments, the fluorosurfactant is a cationic surfactant.

In certain embodiments, the cationic surfactant is selected from the group consisting of amino, amido, ammonio, sulfonamido salts, and mixtures thereof.

In certain embodiments, the fluorosurfactant is an amphoteric surfactant.

In certain embodiments, the amphoteric surfactant is selected from the group consisting of carboxybetaine, sulfobetaine, sulfatobetaine, and mixtures thereof.

In certain embodiments, the fluorosurfactant is a nonionic surfactant.

In certain embodiments, the nonionic surfactant is selected from the group consisting of oxyethylated phenols, oxyethylated alcohols, polyhydric alcohols, and mixtures thereof.

DETAILED DESCRIPTION OF THE INVENTION

As described above, in order to address the problem of insufficient biodegradability of perfluorinated surfactants, the present invention provides biodegradable fluorosurfactants derived from olefins having —CHR, —CHRf, —CHF, and/or —CH$_2$ groups, where R is an alkyl group and Rf is a perfluoro or fluroroalkyl group. Preferably, the —CHR, —CHRf, —CHF, and/or —CH$_2$ groups are contained within partially fluorinated alkenes.

In accordance with the present invention, each of the four major classes of surfactants—anionic, cationic, amphoteric and nonionic—may be prepared. Example anionic surfactants include carboxylates, sulfonates, sulfates, and phosphates; example cationic surfactants include amino, amido, ammonio, and sulfonamido salts; example amphoteric surfactants include carboxybetaine, sulfobetaine, and sulfatobetaine; and example nonionic surfactants include oxyethylated phenols, as well as oxyethylated and polyhydric alcohols. General examples for each of these surfactants are provided below:

1) RfCO$_2^-$ Na$^+$/RF SO$_3^-$ Na$^+$,
2) RfC(O)NH(CH$_2$)$_3$ N$^+$ CH$_3$I$^-$,
3) RfXYN$^+$(CH$_3$)$_2$(CH$_2$)CO$_2^-$/SO$_3^-$/OSO$_3^-$, and
4) RfCH$_2$O(CH$_2$CH$_2$O)$_n$H, respectively.

wherein n is an integer and Rf is F-alkyl group comprising at least one hydrogen, and having a straight or branched chain.

Preferably, the above fluorosurfactants are derived from a number of fluoroolefins (X) that are available at Honeywell or from commercial vendors. Examples include $CF_3CF=CH_2$ (HFO-1234yf), $CF_3CH=CHF$ (HFO-1234ze), $CF_3CF=CHF$ (HFO-1225yf), $CF_3CH=CHCl$ (HCFO 1233zd), $CF_3CH=CH_2$, $CF_3CH=CF_2$, $CF_2=CFCl$, $CH_2=CHF$, $CHF=CHF$, $CH_2=CF_2$, $CF_3CH=CHCF_3$, $CF_3CF=CF_2$, $CF_3CF=CFCF_3$, $CF_3C=H$, $(CF_3)_2CF-CF=CFCF_3$ (HFP dimer), $CF_3CH=CH$, $(CF(CF_3)(CF_2H)$ H, and hexfluoropropene trimer. Such surfactants can be prepared using procedures similar to those detailed on pages 1-21 of Kissa, which is incorporated herein by reference.

In accordance with one embodiment of the present invention, alcohols derived from the above olefins for example, $CF_3CFHCF_2CH_2OH$ and $(CF_3)_2CF-CFH-CF(CF_3)CH_2OH$, can also be employed. As shown in Equation 1, short chain perfluoroalkyl iodides Rf—I ($Rf=CF_3$, $C_2F_5$, $C_3F_7$, $C_4F_9$) can be added to these olefins in the presence of a radical initiator such as ditertiary butyl peroxide, AIBN, benzoyl peroxide or UV light to afford the adduct:

$$Rf-I + X \rightarrow Rf-[X]_n-I \quad \text{(Eq. 1)}$$

wherein $Rf=CF_3$, $C_2F_5$, $C_3F_7$ or $C_4F_9$ and $X=CF_3CF=CH_2$ (HFO-1234yf), $CF_3CH=CHF$ (HFO-1234ze), $CF_3CF=CHF$ (HFO-1225yf), $CF_3CH=CHCl$ (HCFO 1233zd), $CF_3CH=CH_2$, $CF_3CH=CF_2$, $CF_2=CFCl$, $CH_2=CHF$, $CHF=CHF$, $CH_2=CF_2$, $(CF_3)_2CF-CF=CF(CF_3)$, $CF_3CF=CF_2$, $CF_3CH=CH(CF(CF_3)(CF_2H)H$, or hexfluoropropene trimer. X includes all isomers.

In accordance with a second embodiment of the present invention, a useful class of precursors for surfactants is alcohols. Alcohol derivatives of X compounds can be made by the addition of methanol to olefins (see Equation 1a) or from compounds of formula $$Rf[X]_n-[(CH_2-CH_2)]_mI:$$

$$X + CH_3OH \rightarrow H-X-CH_2OH \quad \text{(Eq. 1a)}$$

wherein X is as defined in Equation 1.

In accordance with a third embodiment of the present invention, ethylene can be added to compounds of formula $Rf-[X]_n-I$ to afford ethylenated product as given below in Equation 2:

$$Rf-[X]_n-I + CH_2=CH_2 \rightarrow Rf-[X]_n-[(CH_2-CH_2)]_mI \quad \text{(Eq. 2)}$$

wherein m=1 or 2. Various conditions can be employed to get the desired number of m.

Compounds of formula $Rf-[X]_n-[(CH_2-CH_2)]_mI$ can be converted to various classes of surfactants by functionalizing with various hydrophilic groups (Y) including carboxylates, sulfonates, phosphates, ammonium salts, various betaines, ethoxylated alcohol and the like as shown in Equation 2a, and as described on pages 29-79 of Kissa, which is incorporated herein by reference:

$$Rf-[X]_n-[(CH_2-CH_2)]_mI \rightarrow Rf-[X]_n-CH_2-Y \quad \text{(Eq. 2a)}$$

wherein Y=a carboxylate, sulfate, sulfonate, phosphate, quaternary ammonium, carboxybetaine, sulfobetaines, sulfatobetaine, phosphatobetaine, or alcohol group.

Representative examples include:
$Rf-[X]_n-CH_2-CO_2H$; $Rf-[X]_n-CH_2-CO_2Na$;
$Rf-[X]_n-CH_2-SO_3H$; $Rf-[X]-CH_2-SO_3Na$; $Rf-[X]_n-CH_2-OP(O)(OH)_2$;
$Rf-[X]_n-CH_2-CH_2-N^+(CH_3)_3I^-$; $Rf[X]_n-CH_2CH_2SO_2NH(CH_2)_3N^+(CH_3)_3I^-$;
$Rf-[X]_n-CH_2CH_2N^+(CH_3)_2CH_2CO_2^-$; $Rf-[X]_n-CH_2CH_2SCH_2CH_2N(CH_3)_2{}^+CH_2CO_2^-$;
$Rf-[X]_n-CH_2-O(CH_2CH_2O)_nH$; and, $Rf-[X]_n-CONH(CH_2)_3N(CH_2CH_2O)H$, wherein n in the above formulae denotes an integer.

In accordance with a fourth embodiment of the present invention, preparation of carboxylic acids can be achieved by converting the F-alkyl iodides to the respective alcohol, which is then oxidized to carboxylic acid (see Equation 3) with a suitable reagent such as $HNO_3$, and alternatively, the iodides can also be converted to acid with a reagent combination of $K_2Cr_2O_7/H_2SO_4$ (see Equation 4):

$$Rf-[X]_n-CH_2CH_2I \rightarrow Rf-[X]_n-CH_2CH_2OH \rightarrow Rf-[X]_n-CH_2CO_2H \quad \text{(Eq. 3)}$$

$$Rf-[X]_n-CH_2CH_2I(K_2Cr_2O_7/H_2SO_4) \rightarrow Rf-[X]_n-CH_2CO_2H \quad \text{(Eq. 4)}$$

Respective salts can be obtained by treating the acids with sodium or potassium hydroxide, and F-alkyl iodides can be converted to sulfonic acids by many well established methods in the art.

In accordance with a fifth embodiment of the present invention, as shown in Equations 5 and 6, cationic surfactants are prepared by different methods known in the art, e.g., by treating sulfonyl chloride halide with an amine and then quaternizing with an alkyl halide.

$$Rf-[X]-CH_2CH_2SO_2Cl + (CH_3)_2N(CH_2)_3NH_2 \rightarrow Rf-[X]-CH_2CH_2SO_2NH(CH_2)_3N(CH_3)_2 \quad \text{(Eq. 5)}$$

$$Rf-[X]-CH_2CH_2SO_2NH(CH_2)_3N(CH_3)_2 + CH_3I \rightarrow Rf-[X]-CH_2CH_2SO_2NH(CH_2)_3N^+(CH_3)_3I^- \quad \text{(Eq. 6)}$$

In accordance with a sixth embodiment of the present invention, amphoteric surfactants such as betaines are prepared as shown in Equations 7 and 8. For example, carboxy betaines may be prepared by treating F-alkyl tertiaryamine with chloro acetic acid or its sodium salt. Carboxy-betaines with sulfide linkage may be prepared by treating F-alkyl iodide with (2-mercaptoethyl)dimethylammonium chloride and subsequent quaternization with chloroacetic acid.

$$Rf-[X]-CH_2CH_2I + HSCH_2CH_2N(CH_3)_2 \cdot HCl + NaOH \rightarrow Rf-[X]-(CH_2)_2SCH_2CH_2N(CH_3)_2 \quad \text{(Eq. 7)}$$

$$Rf-[X]-(CH_2)_2SCH_2CH_2N(CH_3)_2 + ClCH_2CO_2H \rightarrow Rf-[X]-(CH_2)_2SCH_2CH_2N^+(CH_3)_2CH_2CO_2^- \quad \text{(Eq. 8)}$$

As shown in Equation 9, nonionic F-alkyl surfactants can be prepared by straight forward oxyethylenation in the presence of catalyst, for example, boron trifluoride ($BF_3$ cat).

$$Rf-[X]-CH_2CH_2OH + \text{Ethylene oxide} + (BF_3 \text{ cat}) \rightarrow Rf-[X]-CH_2CH_2O(CH_2CH_2O)_nH \quad \text{(Eq. 9)}$$

EXAMPLES

Example 1

Addition of $C_2F_5I$ to $CF_3CH=CHF$

Into a clean, dry and evacuated 650 ml autoclave (Parr® reactor) was added ditertiarybutyl peroxide (10.5 g) and $C_2F_5I$ (75 g). The autoclave was then cooled with dry ice and condensed 65 g $CF_3CH=CHF$. The reactor was brought to room temperature and heated to and maintained at 145° to 150° C. for 6 hrs; the reactor was then brought to room temperature, vented of volatile materials, and the contents in the autoclave were poured into cold water. The separated organic phase was washed with 5% aq. sodium bisulphite (20 mL), water (20 mL) and brine (20 mL), dried (MgSO$_4$), and distilled to afford CF$_3$CF$_2$[CHF—CH(CF$_3$)]—I (n=1).

Example 2

The reaction was conducted in the same manner as in Example 1, except that CF$_3$CF=CHF was used instead of CF$_3$CH=CFH to afford CF$_3$CF$_2$[CHF—CF(CF$_3$)]$_n$—I (n=1).

Example 3

The reaction of C$_2$F$_5$I with CF$_3$CF=CH$_2$, CF$_3$H=CH$_2$, CF$_2$=CFCl, CF$_3$CF=CF$_2$, (CF$_3$)$_2$CF—CF=CF(CF$_3$), CF$_3$CH=CH(CH(CF$_3$)(CF$_2$H)) were carried out as in example 1, and the following compounds were obtained: CF$_3$CF$_2$[CF$_3$CF—CH$_2$]$_n$—I, CF$_3$CF$_2$[CF$_3$CH—CH$_2$]$_n$—I, CF$_3$CF$_2$[CF$_2$—CFCl]$_n$—I, CF$_3$CF$_2$[CF$_2$—CF(CF$_3$)]$_n$—I, CF$_3$CF$_2$[(CF$_3$)CF—C(C$_2$F$_5$)—CF(CF$_3$)$_2$]$_n$—I (isomers), and CF$_3$CF$_2$[(CF$_3$)CH—CH—(CF(CF$_3$)(CF$_2$H))]$_n$—I (all n=1).

Example 4

Insertion of Ethylene into C—I bond in CF$_3$CF$_2$[CHF—CH(CF$_3$)]$_n$—I (n=1)

A 400 mL autoclave was charged with CF$_3$CF$_2$[CHF—CH(CF$_3$)]$_n$—I (n=1) (72 g, 0.2 mol), ethylene (6.25 g, 0.13 mol) and D (+)-limonene (0.4 g) and the reactor was heated at 240° C. for 12 hours. The product formed was then transferred and distilled under reduced pressure to afford CF$_3$CF$_2$[CHF—CH(CF$_3$)]$_n$—(CH$_2$—CH$_2$)$_m$—I (n=m=1) as the major product (60%).

Example 5

In a similar manner, ethylenated compounds were prepared for CF$_3$CF$_2$[CF$_3$CF—CH$_2$]$_n$—I, CF$_3$CF$_2$[CF$_3$CH—CH$_2$]$_n$—I, CF$_3$CF$_2$[CF$_2$—CFCl]$_n$—I, CF$_3$CF$_2$[CF$_2$—CF(CF$_3$)]$_n$—I, CF$_3$CF$_2$[(CF$_3$)CF—C(C$_2$F$_5$)—CF(CF$_3$)$_2$]$_n$—I (isomers), CF$_3$CF$_2$[(CF$_3$)CH—CH—(CF(CF$_3$)—(CF$_2$H))]$_n$—I by following the procedure of Example 4.

Example 6

Conversion of CF$_3$CF$_2$[CHF—CH(CF$_3$)]$_n$—(CH$_2$—CH$_2$)$_n$—I (n=m=1) to CF$_3$CF$_2$[CHF—CH(CF$_3$)]$_n$—(CH$_2$—CH$_2$)$_m$—SO$_3$Na A 500 mL flask equipped with a stirrer, condenser, a mixture of CF$_3$CF$_2$[CHF—CH(CF$_3$)]—(CH$_2$—CH$_2$)$_m$—I (n=m=1) (0.2 mol), ethanol (100 mL), water (100 mL), sodium sulfite (0.4 mol) and copper powder (4.8 g) was refluxed under nitrogen for a week. After this, 250 mL water was added, mixed well and filtered. The filtrate was cooled and crystallized/precipitated using sodium salt, and CF$_3$CF$_2$[CHF—CH(CF$_3$)]$_n$—(CH$_2$—CH$_2$)$_m$—SO$_3$Na was separated by filtration and dried (0.15 mol, 75%).

Example 7

Conversion of CF$_3$CF$_2$[CHF—(CF$_3$)CH]—I to CF$_3$CF$_2$[CHF—(CF$_3$)CH]$_n$—CH$_2$CO$_2$H/Na (n=1)

Conversion of CF$_3$CF$_2$[CHF—(CF$_3$)CH]—I to CF$_3$CF$_2$[CHF—(CF$_3$)CH]$_n$—CH$_2$CO$_2$H was effected as described in J. Fluorine Chem. 66, (1994), 249-252, incorporated herein by reference. Thus, CF$_3$CF$_2$[CHF—(CF$_3$)CH]$_n$—I was reacted with vinyl acetate to CF$_3$CF$_2$[CHF—(CF$_3$)CH]$_n$—CH$_2$CHIOCOCH$_3$, which was then hydrolyzed to aldehyde, CF$_3$CF$_2$[CHF—(CF$_3$)CH]$_n$—CH$_2$CHO, and finally oxidized to the desired acid, CF$_3$CF$_2$[CHF—(CF$_3$)CH]$_n$—CH$_2$CO$_2$H. The acid was converted to its sodium salt by treating with equimolar amount of NaOH in water. In a similar fashion, by employing the above procedure other iodides were converted to the respective acids/salts.

Example 8

Conversion of CF$_3$CF$_2$[CHF—(CF$_3$)CH]$_n$—[CH$_2$CH$_2$]$_m$I (n=m=1) to betaine derivative CF$_3$CF$_2$[CHF—(CF$_3$)CH]$_n$—[CH$_2$CH$_2$]$_m$N$^+$(CH$_3$)$_2$CH$_2$CO$_2$HCl$^-$ Part A: A solution of dimethylamine (0.025 mol) (33% in ethanol) and CF$_3$CF$_2$[CHF—(CF$_3$)CH]$_n$—[CH$_2$CH$_2$]$_m$—I (0.02 mol) was added to sodium carbonate (0.2 mol) in ethanol and water (60 mL+15 mL) solution and refluxed for 24 hours. After this the reaction mixture was filtered, the filtrate was washed with water (10 ml), extracted in ether (50 mL), and dried (Na$_2$SO$_4$) to afford the crude amine derivative which was distilled to afford CF$_3$CF$_2$[CHF—(CF$_3$)CH]$_n$—CH$_2$CH$_2$]$_m$N(CH$_3$)$_2$.

Part B: Subsequently, a stirred mixture of CF$_3$CF$_2$[CHF—(CF$_3$)CH]$_n$—[CH$_2$CH$_2$]$_m$N(CH$_3$)$_2$ (0.01 mol) and monochloro acetic acid (0.01 mol) was slowly heated (120° to 130° C.) for an hour in an oil bath to afford the product CF$_3$CF$_2$[CHF—(CF$_3$)CH]$_n$—[CH$_2$CH$_2$]$_m$N$^+$(CH$_3$)$_2$CH$_2$CO$_2$HCl$^-$.

Example 9

Preparation of CF$_3$CF$_2$[CHF—(CF$_3$)CH]$_n$—CH$_2$CH$_2$]$_m$SCH$_2$CH$_2$N$^+$(CH$_3$)$_2$CH$_2$CO$_2$HCl (n=m=1)

Part A: To a stirred solution of NaOH (4.0 g, 0.1 mol) in absolute ethanol (50 mL) was added 0.05 mol of 2-dimethylaminoethylthiohydrochloride, and the mixture was heated to 50° C. for 15 minutes. This solution was then added to a solution of CF$_3$CF$_2$[CHF—(CF$_3$)CH]$_n$I (0.05 mol) in 100 mL tertiaryamyl alcohol and the mixture was refluxed for 6 hours. After cooling to room temperature, the reaction mixture was filtered, concentrated on a rotavap, and the residue extracted with ether (2×150 mL). The combined ether extracts were washed with 150 ml 5% aqueous NaOH, 100 mL water, dried (MgSO$_4$), and concentrated under reduced pressure to give a liquid residue—the crude CF$_3$CF$_2$[CHF—(CF$_3$)CH]SCH$_2$CH$_2$N(CH$_3$)$_2$—which could be purified via distillation.

Part B: The reaction was conducted exactly the same manner as described in Example 8, part B, except that CF$_3$CF$_2$[CHF—(CF$_3$)CH]$_n$SCH$_2$CH$_2$N(CH$_3$)$_2$ was used in place of CF$_3$CF$_2$[CHF—(CF$_3$)CH]—[CH$_2$CH$_2$]$_m$N(CH$_3$)$_2$ to afford CF$_3$CF$_2$[CHF—(CF$_3$)CH]$_n$—[CH$_2$CH$_2$]$_m$SCH$_2$CH$_2$N$^+$(CH$_3$)$_2$CH$_2$CO$_2$HCl$^-$.

Example 10

Conversion of (CF$_3$)$_2$CF—CFH—(CF$_3$)CF—CH$_2$OH to (CF$_3$)$_2$CF—CFH—(CF$_3$)CF—CH$_2$O—CH$_2$CH$_2$OH Part A: Ethylene oxide (12.1 mmol) was allowed to react in diethyl ether with 32 mmol (CF$_3$)$_2$CF—CFH—(CF$_3$)CF—

$CH_2OH$ in ether with $BF_3$ etherate complex (3.0 g) as the catalyst for 10 min at room temperature. The reaction mixture was concentrated, extracted in ether, washed with 2% NaOH, washed with water, and dried to afford $(CF_3)_2CF$—CFH—$(CF_3)CF$—$CH_2O$—$CH_2CH_2OH$.

Part B: Ethylene oxide (12.1 mmol) was allowed to react in diethyl ether with dehydrated alumina (10 g) and 32 mmol $(CF_3)_2CF$—CFH—$(CF_3)CF$—$CH_2OH$ for 10 min at room temperature. Filtration and work up afforded $(CF_3)_2CF$—CFH—$(CF_3)CF$—$CH_2O$—$CH_2CH_2OH$.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A fluorosurfactant having the general formula

Rf—X—Y wherein Rf is a perfluorinated alkyl group;
   wherein X is derived from a partially fluorinated alkene;
   Y is a neutral group or a hydrophilic group;
   wherein the partially fluorinated alkene is selected from the group consisting of $CF_2$=CFCl, $CH_2$=CHF, CHF=CHF, $CH_2$=$CF_2$, $CF_3CH$=$CHCF_3$, $CF_3CF$=$CFCF_3$, $CF_3C$=H, and $(CF_3)_2CF$—CF=$CFCF_3$ (HFP dimer);
   and wherein the surfactant is biodegradable.

2. The fluorosurfactant of claim 1, wherein X is derived from a partially fluorinated propene.

3. A fluorosurfactant having the general formula

Rf—X—Y wherein Rf is a perfluorinated alkyl group;
   wherein X is derived from a partially fluorinated alkene;
   Y is a neutral group or a hydrophilic group;
   wherein the partially fluorinated propene is selected from the group consisting of $CF_3CF$=$CH_2$ (HFO-1234yf), $CF_3CH$=CHF (HFO-1234ze), $CF_3CF$=CHF (HFO-1225yf), $CF_3CH$=CHCl (HCFO 1233zd), $CF_3CH$=$CH_2$, $CF_3CH$=$CF_2$, $CF_3CF$=$CF_2$, $CF_3CH$≡CH, $(CF(CF_3)(CF_2H)H$, and hexafluoropropene trimer.

4. The fluorosurfactant of claim 1, further comprising an anionic surfactant.

5. The fluorosurfactant of claim 4, wherein the anionic surfactant is selected from the group consisting of carboxylates, sulfonates, sulfates, phosphates, and mixtures thereof.

6. The fluorosurfactant of claim 1, further comprising a cationic surfactant.

7. The fluorosurfactant of claim 6, wherein the cationic surfactant is selected from the group consisting of amino, amido, ammonio, sulfonamido salts, and mixtures thereof.

8. The fluorosurfactant of claim 1, further comprising an amphoteric surfactant.

9. The fluorosurfactant of claim 8, wherein the amphoteric surfactant is selected from the group consisting of carboxybetaine, sulfobetaine, sulfatobetaine, and mixtures thereof.

10. The fluorosurfactant of claim 1, further comprising a nonionic surfactant.

11. The fluorosurfactant of claim 10, wherein the nonionic surfactant is selected from the group consisting of oxyethylated phenols, oxyethylated alcohols, polyhydric alcohols, and mixtures thereof.

12. The fluorosurfactant of claim 3, further comprising an anionic surfactant.

13. The fluorosurfactant of claim 12, wherein the anionic surfactant is selected from the group consisting of carboxylates, sulfonates, sulfates, phosphates, and mixtures thereof.

14. The fluorosurfactant of claim 3, further comprising a cationic surfactant.

15. The fluorosurfactant of claim 14, wherein the cationic surfactant is selected from the group consisting of amino, amido, ammonio, sulfonamido salts, and mixtures thereof.

16. The fluorosurfactant of claim 3, further comprising an amphoteric surfactant.

17. The fluorosurfactant of claim 16, wherein the amphoteric surfactant is selected from the group consisting of carboxybetaine, sulfobetaine, sulfatobetaine, and mixtures thereof.

18. The fluorosurfactant of claim 3, further comprising a nonionic surfactant.

19. The fluorosurfactant of claim 18, wherein the nonionic surfactant is selected from the group consisting of oxyethylated phenols, oxyethylated alcohols, polyhydric alcohols, and mixtures thereof.

* * * * *